(12) United States Patent
Kelley

(10) Patent No.: US 11,621,064 B1
(45) Date of Patent: *Apr. 4, 2023

(54) BI-DIRECTIONAL INTERFACE SYSTEM AND METHOD FOR SEAMLESS EXCHANGE

(71) Applicants: Tiffany Kelley, Boston, MA (US); Nightingale Apps LLC, Boston, MA (US)

(72) Inventor: Tiffany Kelley, Boston, MA (US)

(73) Assignee: NIGHTINGALE APPS LLC, Boston, MA (US)

( * ) Notice: Subject to any disclaimer, the term of this patent is extended or adjusted under 35 U.S.C. 154(b) by 203 days.

This patent is subject to a terminal disclaimer.

(21) Appl. No.: 17/120,493

(22) Filed: Dec. 14, 2020

Related U.S. Application Data

(63) Continuation of application No. 14/292,208, filed on May 30, 2014, now Pat. No. 10,867,694.

(60) Provisional application No. 61/830,013, filed on May 31, 2013.

(51) Int. Cl.
*G16H 10/60* (2018.01)
(52) U.S. Cl.
CPC .................................. *G16H 10/60* (2018.01)
(58) Field of Classification Search
None
See application file for complete search history.

(56) References Cited

U.S. PATENT DOCUMENTS

| | | | |
|---|---|---|---|
| 6,421,650 | B1 | 7/2002 | Goetz et al. |
| 9,378,380 | B1 | 6/2016 | Reid et al. |
| 2005/0251417 | A1* | 11/2005 | Malhotra .............. G16H 10/60 |
| | | | 705/2 |
| 2006/0287890 | A1* | 12/2006 | Stead ..................... G16H 10/20 |
| | | | 705/3 |
| 2007/0035403 | A1 | 2/2007 | Krishna et al. |
| 2007/0043594 | A1* | 2/2007 | Lavergne .............. G06Q 10/10 |
| | | | 705/64 |
| 2008/0051679 | A1 | 2/2008 | Maljanian |
| 2009/0138285 | A1* | 5/2009 | Denberg ................ G16H 10/60 |
| | | | 707/E17.014 |

(Continued)

FOREIGN PATENT DOCUMENTS

CN    103578070 A    2/2014

*Primary Examiner* — Robert W Morgan
*Assistant Examiner* — Edward B Winston, III
(74) *Attorney, Agent, or Firm* — Honigman, LLP

(57) ABSTRACT

A bi-directional interface system that facilitates exchange of personal health information ("PHI") between a mobile device and an electronic health record ("EHR") system and/or other ancillary systems without storing information on the mobile device. The system may display data that exists in the EHR and/or other ancillary systems valuably viewed at a glance (e.g., vital signs, weight, last void data), as well as facilitate data entry that would feed into the EHR (e.g., vital signs and intake and output). The system may customize at a unit level and/or professional role the information available to health care professionals at the critical time of handoffs and reduce the health care professional's individual need to rely on memory or handwritten notes, further reducing missed information or erroneous information opportunities. The system may provide a mobile application to view and enter patient data to reduce potentially delayed information and treatments of care.

20 Claims, 7 Drawing Sheets

(56) References Cited

U.S. PATENT DOCUMENTS

| | | | |
|---|---|---|---|
| 2010/0332404 A1 | 12/2010 | Valin | |
| 2012/0035959 A1* | 2/2012 | Berdia | G16H 10/60 |
| | | | 705/3 |
| 2012/0066393 A1 | 3/2012 | Tekwani | |
| 2012/0232929 A1* | 9/2012 | Experfon | G06Q 10/06 |
| | | | 705/3 |
| 2012/0303386 A1* | 11/2012 | Zavaleta | G16H 40/67 |
| | | | 705/3 |
| 2013/0110547 A1* | 5/2013 | Englund | G16H 10/60 |
| | | | 705/3 |
| 2013/0191513 A1* | 7/2013 | Kamen | H04L 67/02 |
| | | | 709/219 |

* cited by examiner

Figure 2

Figure 5 tesing notes

BI-DIRECTIONAL INTERFACE SYSTEM AND METHOD FOR SEAMLESS EXCHANGE

PRIORITY CLAIM

This application is a continuation of prior U.S. patent application Ser. No. 14/292,208, filed May 30, 2014, which claims the benefit of prior U.S. Provisional Patent Application No. 61/830,013, filed on May 31, 2013, each of which is hereby incorporated by reference in its entirety.

TECHNICAL FIELD

The present invention is directed to a bi-directional interface system that facilitates the seamless exchange of personal health information ("PHI") between a mobile device and an associated healthcare organization's electronic health record (EHR) system and/or other ancillary systems without storing any PHI on the mobile device. The bi-directional interface system is designed to support the information workflow needs of nurses and other health care professionals.

BACKGROUND

While electronic health records ("EHRs") are expected to improve the accuracy, efficiency, timeliness, and safety of patient care, opportunities remain to enhance the exchange of information between caregivers regardless of the physical location of the nurse and/or health care professional. Nurses and health care professionals are often "on-the-go" or "mobile" in the provision of patient care. Yet, the access to electronic information within health care organizations often is only accessible through computer workstations that are not mobile in nature. The nurse and/or other health care professionals must locate an available computer to exchange information needed for care. As a result, the actual exchange of information through EHRs and/or ancillary data repository systems can be sub-optimal with regard to accuracy, efficiency, timeliness, and safety. Accordingly, a bi-directional interface system is necessary that may provide nurses and other health care professionals with critical information needed to provide safe patient care in a manner that is tailored to integrate with the daily workflow needs of the nurse and/or other health care professional.

For example, nurses are the largest group of health care professionals working in hospital settings. Nurses primarily are employed by a nursing unit that has a set number of available beds for admitting patients and a set of criterion for the patient to be admitted to the nursing unit. The criterion may include, but is not limited to, the diagnosis, service (e.g., medicine, surgery, pediatrics), and acuity level of the patient. Nurses typically work 12 hours per day when providing direct patient care. As a result, each patient will have at least 2 nurses in a 24-hour period. The transfer of care responsibility from one nurse to another is often referred to as a patient handoff. During the patient handoff, the nurse may provide a verbal description of specific patient information that the next nurse will need to know in order to provide safe, high quality care to the patient over the next shift. During the verbal description, the oncoming nurse, who will be assuming care responsibility for the patient, may write down information based on the verbal information that is being communicated by the off-going nurse. The information that is written down is temporarily stored on a piece of paper that is not part of the patient's official medical record.

The nursing handoff process is the first step in the nurse's gathering of patient information needed to provide care for that day. However, handoffs typically have frequent interruptions, high noise levels, and are highly reliant on the nurse's individual memory to communicate information deemed necessary by the nurse who worked the past 12 hours. In addition to the nurse's memory, the nurse will refer to the piece of paper, often called the nurse's "brain", to communicate information needed to know the patient. The nurse who is beginning his/her workday will listen to what the nurse is communicating and temporarily store the communicated information on his/her own paper "brain". The nurses will use their paper "brains" to temporarily store the information and organize their day for their patients. Their paper "brains" are kept with them at all times, often in their pocket, and are referenced frequently throughout the course of the day. The current workflow described above has inherent system limitations to the quality of care provided to patients. The handoff process is one in which omitted, missed, and or erroneous verbal communication of information about the patient can lead to potential medical errors. Over 50% of sentinel events have been tied to communication failures.

A mobile application is necessary that will address these limitations in the current workflow by eliminating the individualized paper-based "brain" and minimizing the reliance on one individual's memory to relay the information needed to care for a patient. Specifically, such a mobile application should visually display the specific information needed to care for patients located on a patient care unit. For the non-nursing health care professionals, the design may be unit-based, or health care professional role based (e.g., nursing assistant, social worker, nutritionist) depending upon the health care organizations structure and processes for the health care professionals. An example of a role-based design may be for a role that consults with patients on multiple care units each day (e.g., physical therapist, nutritionist). In this instance, the unit-based design may be limited for that role.

SUMMARY

In general, this invention describes a bi-directional interface software system which facilitates the seamless exchange of personal health information. The system will address the limitations in the current patient care workflow by eliminating the individualized paper-based "brain" and minimizing the reliance on one individual's memory to relay the information needed to care for a patient. Additionally, the bi-directional interface software system will increase the standardization of information across caregivers in an effort to reduce errors. Furthermore, the system's technical architecture is designed in such a way as to minimize potential breaches in privacy and security of personal health information. As such, the system may access the patient information available within a patient's EHR and/or other ancillary systems, and may display such information via a mobile device, without storing any of the information on the mobile device itself. Accordingly, the system prevents any personal health information messages from going outside of the firewalls (external, internal, and data).

The system may utilize a software application that may be available for use on a mobile device, which may visually display the specific information needed to care for patients, for example, by generating and displaying images on the mobile device. The advantage of the mobile device is such that it allows for portable usage by nurses and other health care professionals. The mobile device may include, but is not limited to devices such as: iPhones, iTouch, iPad, Android devices (Kindle, Nook, Samsung devices), tablets, laptops and/or any other future technology not otherwise currently commercially identified, that can easily be transported from one location to another. Accordingly, the system may include software that is flexible enough for customization that allows for different patient care units to make changes that do not affect other care units. For example, the information needs of nurses working on a cardiac unit may require specific data and information about the patient that is not necessary on an orthopedic unit. The system may provide a visual display of data interfaced from the electronic health record ("EHR") and/or any other pertinent ancillary database. Furthermore, to minimize potential breaches in privacy and security, the system is designed so that patient information that is viewed and transmitted through the system does not get stored onto any devices used by the nurses or other healthcare professionals.

The bi-directional interface system may provide nurses and other health care professional roles with critical information needed to provide safe patient care in a manner that is tailored to integrate with their daily information workflow needs. The other health care professions may include, but are not limited to, nursing assistants, ancillary support staff, physical therapists, occupational therapists, social workers, etc. The invention will solve a current problem that has the ability to impact the delivery of safe, error free care that is accurate, efficient, and delivered in a timely manner.

The invention may be designed in such a way to allow for clients to customize the system at a unit-based level for nurses and at a unit level or role-oriented level for other health care professionals. For example, the practice of nursing handoffs varies from unit to unit and the specific information needs generally vary per unit and health care role (e.g., nurses, nursing assistant, ancillary support staff). The system may allow individual care units to determine what data elements will be displayed, rather than at an entire hospital organizational level. Additionally, in an alternative embodiment, the system may be designed to be role-based, in that the specific data elements to be displayed will be customized based on the specific role of the health care professional utilizing the system. The role-based design may incorporate some elements of the unit-based design.

Furthermore, the system may allow for bi-directional interfaces to and from the electronic health record (EHR) and/or other ancillary systems with specific logic built into the mobile application based on the information needs of nurses and other health care professionals. The system may display data that exists in the EHR and/or other ancillary database systems that would be valuable to easily view at a glance (e.g., vital signs, weight, last void), as well as facilitate data entry that would interface into the EHR (e.g., vital signs and intake and output). Accordingly, the system may standardize the information available to nurses and other health care professionals at the critical time of handoffs, and may reduce the individual's need to rely on memory, handwritten notes, and reduce the potential for missed or erroneous exchange of information. Furthermore, the system may provide an accessible application to view and enter pertinent patient data to reduce the potential for delayed information entry and delayed treatments of care. Additionally, the information needs of other health care professionals may require customization based on the specialty of practice in the role (e.g., therapists, social workers, providers) and designation of patients requiring care. For example, a physical therapist may be assigned patients on multiple care units. The information needs and workflow of the physical therapist may differ from that of the nurse based on the scope of practice for both health care professionals. While electronic health records ("EHRs") are expected to improve the accuracy, efficiency, timeliness, and safety of patient care, the actual exchange of information through EHRs can be sub-optimal with regard to those four areas (accuracy, efficiency, timeliness, and safety). Part of the limitations is due to the large reliance on verbal communication between caregivers and the individualized designation of essential information needs by the nurse during handoffs.

The system will facilitate more efficient extraction of data from EHRs and/or ancillary systems. The system will also facilitate the efficient entry of data (when appropriate) for timeliness in the health care teams' decision-making process. The health care teams are often relying on specific data elements collected and communicated through the EHR and/or ancillary systems in order to evaluate a patient's condition, and make modifications to the patient's plan of care or recognizing when a patient may be in distress and in need of more aggressive treatment. The support of the bi-directional interface software system on mobile devices will allow for the nurse and other health care professionals to access patient information and enter patient information from any location that supports the application on the device within the health care organization. The accuracy will be in the standardized display of information needed for care.

The bi-directional interface system may include a centralized server, a security module, a customization module, a reporting module, a scheduling module, a data trending module, a medication administration record module, an updates module, a notes module, an allergies module and an images module. The centralized server, security module, customization module, reporting module, scheduling module, data trending module, medication administration record module, updates module, notes module, allergies module, images module, electronic health record system and ancillary systems may be integrated with each other. The ancillary systems may include clinical data systems, which may include but are not limited to laboratory information systems, radiology information systems, pharmacy information systems and systems that manage other personal patient related information needed for care delivery. The centralized server may host and may serve the requests of the customization module, the security module, the reporting module, the scheduling module, the data trending module, the medication administration record module, the updates module, the notes module, the allergies module, and the images module. This server may execute the instructions of these modules to perform particular functions.

The system may dynamically extract patient data from an associated electronic health record repository of an electronic health record system and/or other ancillary systems. This patient data may include, but is not limited to, vital signs and intake and output values, clinical documentation, allergies, demographics, etc. Accordingly, the system may generate visual displays of the patient data on a mobile device. The system may automatically update the patient data displayed on the mobile device as said data is updated in said associated electronic health record system and/or other ancillary systems. Furthermore, the system may transmit patient data that is inputted in the application on the mobile device to the associated electronic health record repository in real time. The patient data that is inputted in the application on the mobile device may include, but is not limited to, vital signs and/or intake and output values.

The system may include a security module that securely transmits the patient data over a network. The system's technical architecture is designed in such a way to minimize potential breaches in privacy and security of personal health information. As such, the system may access the patient information available within the patient's EHR, and may display such information via a mobile device, without storing any of the information on the mobile device itself. The system prevents any personal health information messages from going outside of the external firewalls.

The system may include an application that may communicate/login into existing enterprise authentication active directory (ADAM/LDAP) and use push notification services hosted on a system server. The transactions may be facilitated via a secure socket layer SSL/HTTPS/AES 256 encrypted communications. The system server may host vital back-end services for the system application and also hosts local relational database management system (RDBMS) which may include Oracle or (Oracle's MySQL); the majority of the back-end services may be on the RESTful/protocol. After successful authentication from the system application, the system application may fire AJAX (Asynchronous JavaScript and XML) calls to the existing EHR systems and/or other ancillary systems to retrieve relevant information. The EHR system may leverage relational database management systems and may provide asynchronous alerts (push notifications) for Labs/Orders/Other via a "system rules engine" service endpoints. The push notification services may be communicated via a system rules engine into the System Server. A message may be created into RDBMS, and then the system server may create a global unique identifier ("GUID") for that specific message. This will prevent any personal health information ("PHI") message from going outside of the firewall and not achieved on any external servers. The push notification services payload may be sent outside of the firewall to push it into a user's device; no PHI is sent and only GUID is sent with the payload. For example, Apple Push Notification Services "APNS" may push the notifications to the appropriate devices and if the device is within the internal firewall then it can look up the message by communication with the system push notification services (hosted on the system server).

Additionally, a customization module may be utilized to select the specific types of patient data to be extracted based on the nursing care unit and/or health care professional role. The specific information needs generally vary per nursing care unit and health care role (e.g., nurses, nursing assistant, ancillary support staff). The system may allow individual care units and/or other health care professional role groups to determine what data elements and information will be displayed, rather than at an organizational level. Additionally, the system may be designed to be role-based, in that the specific data elements to be displayed will be customized based on the specific role of the health care professional utilizing the system. This role-based design may incorporate some elements of the unit-based design.

In one aspect, the bi-directional interface system may include a reporting module, which may generate a customizable comprehensive report of said patient information for the nurse and other health care professional. This nursing report may include vital patient care information, which may include but is not limited to a patient's name, age, weight, date of birth, date of admission, current admission diagnosis, and allergies. The system-generated report provides system users access to a synthesis of information, extracted from a patient's EHR and organized in a meaningful manner, relevant to the patient population being served and the role of the user.

In another aspect, the system may include an updates module, which may generate a customized report of patient information that has changed from a set period of time for the nurse and/or other health care professionals. For example, a nurse that cared for the patient yesterday may not need to be updated with the entire report from the reporting module. Instead, the updates will provide the nurse with the information that has changed in a designated time frame. The system may also include a notes module, which may be utilized by a user to generate notes to communicate personal aspects about an individual patient's care. The notes module may allow a user to enter short messages that will be saved as reminders of these individual care needs that would be necessary for other nurses and health care professionals. Additionally the system may automatically transmit these notes to a patient's EHR. The current EHR tends to have more structured data fields that are a challenge for inputting short messages about the patient that provides additional context about the patient.

In another aspect, the system may include a scheduling module, which generates and electronically organizes a nurse's schedule of activities. The scheduling module can also be used for the other health care professionals. The system may automatically generate such a schedule, and a user may also manually create a schedule. The bi-directional interface system may also seamlessly transmit messages that are inputted in the application on said mobile device to said associated electronic health record repository. The system may display dynamically updated orders, allergies and/or lab results from the electronic health record (EHR) and/or ancillary systems.

In yet another aspect, the bi-directional interface system may include a data trending module, which interfaces with the EHR and/or ancillary systems to generate trends of patient data. Additionally, the system may include a medication administration record module which is integrated with a patient's medications administration record to generate and display a schedule of medications and/or order details on the mobile device.

In another aspect, the bi-directional interface system may include an images module, which generates and can view images through the mobile device that can be interfaced with the EHR and/or ancillary systems. In another aspect, the system may provide an allergies module, which may display allergies that are recorded in a patient's EHR and/or ancillary system.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The details of one or more embodiments are set forth in the following detailed description of the invention and the accompanying drawings. Other objectives, features, and advantages of the invention will be more readily understood upon consideration of the following Detailed Description of the invention, taken in conjunction with the accompanying drawings, and with the claims.

DESCRIPTION OF THE DRAWINGS

The present invention is further described in the detailed description which follows, in reference to the noted plurality of drawings by way of non-limiting examples of certain embodiments of the present invention, in which like numerals represent like elements throughout the several views of the drawings, and wherein:

FIG. 2 depicts a visual representation of accessing and exchanging patient information.

FIG. 5 depicts a visual representation of a vital signs entry view and display view.

DETAILED DESCRIPTION

Figure 1:
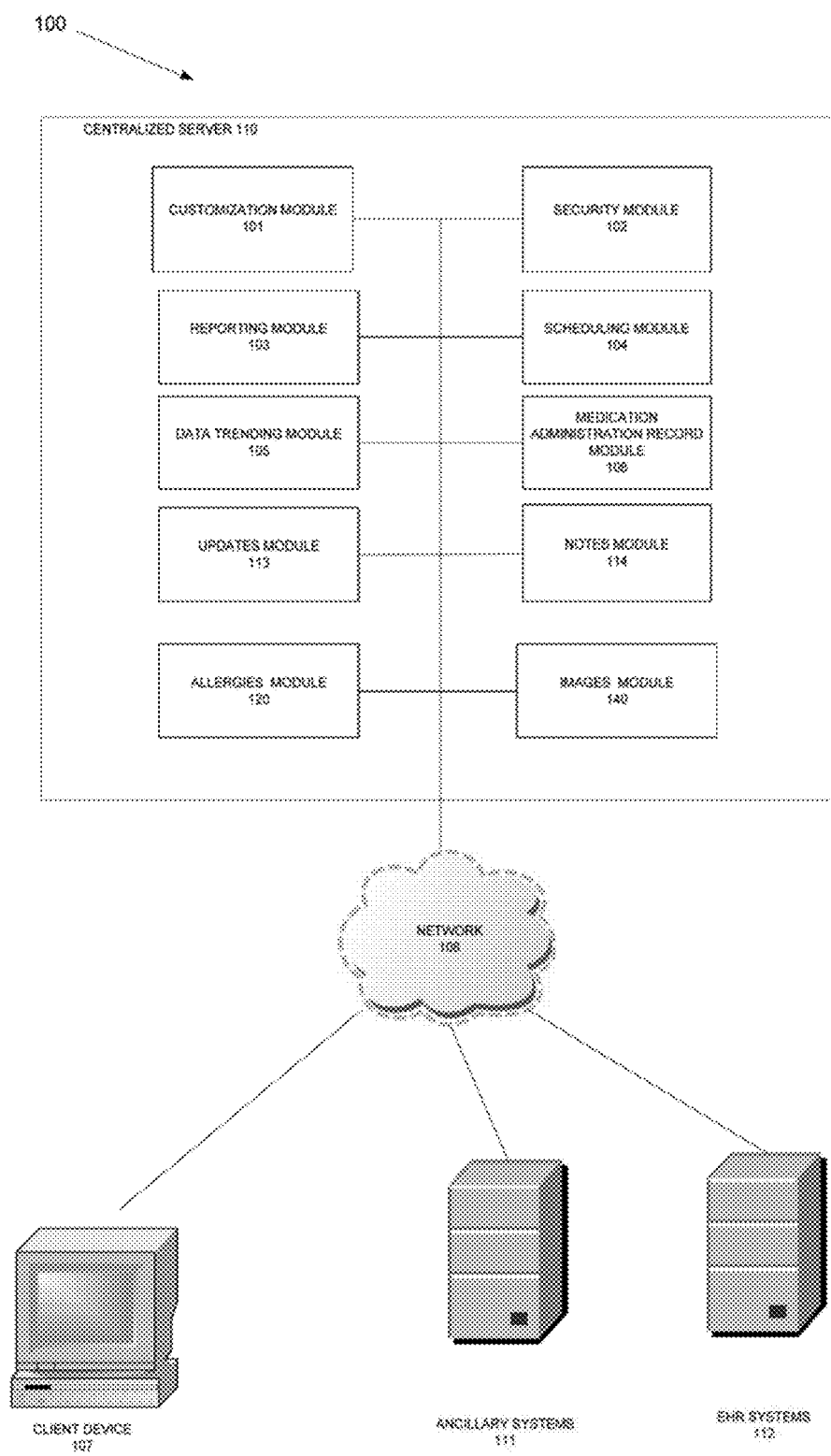
FIG. 1 illustrates and exemplary unit-based bi-directional interface system and its components consisting thereof.

A detailed explanation of the system and method according to the preferred embodiments of the present invention are described below.

The bi-directional interface system provides a software application that facilitates efficient and timely access to current and consistent patient information needed for the provision of safe care to patients in hospital settings. The system provides efficient and timely access to patient information to nurses and other health care professionals in ways that accommodate and support the naturally occurring patient care workflow processes for nurses and other health care professionals in patient settings for safe patient care. For example, the system may provide several capabilities that facilitate efficient and timely access to specific information needs from the beginning to the ending of a nurses' workday. The system may be supported on mobile devices such that a nurse or other health care professional will have access to each patient's information needed for care regardless of the nurse's or other health care professional's physical location on the unit: smart phone, tablet device (iTouch, iPad mini); "mobile cart" (computer designed into a cart or a laptop computer secured onto the cart; and/or stationary computer. The software application may be installed on the mobile devices.

The system seamlessly interfaces with existing EHR and/or other ancillary systems to automatically extract the information needed to provide care to a patient, and may display such information on a mobile device. This information may be collected in the first period of the nurse's workday, "beginning handoff," during a process that nurses refer to as "report." Nurses may describe the information collected during report as providing all of the information needed to provide care to the patient. As the nurse's workday progresses, the patient's condition and care needs are likely to change. Therefore, the collection and communication of patient information needed to know the patient continues after report ("Beginning Handoff") until the end of the nurse's work day when the nurse provides report to the oncoming nurse during "Ending Handoff" who will be the one assuming patient care responsibility. The same format may be used by other health care professionals. The health care professionals will receive a report on their patients from another member of his or her team and maintain that report with him or her until handing over care responsibility to the next individual.

The technical architecture of the system is such that the patient information that is viewed and transmitted through the system does not get stored onto any of the mobile devices, and remains stored in the associated EHR and/or other ancillary systems. The ancillary systems may include clinical data system, which may include but are not limited to laboratory information systems, radiology information systems, pharmacy information systems, and systems that manage other diagnostic information.

In one aspect, the bi-directional interface system may generate and display a list of patients admitted to the inpatient care unit. The system may also generate an individual "my patients" list of the nurse's and/or other health care professional's assigned patients for the day from the unit census list(s). The unit census list may include the complete census for the unit and some basic patient level data, which may include, but is not limited to the patient name, medical record number ("MRN"), and room number. The unit census list may be utilized by the system to automatically to create the individual nurse's list of assigned patients. The system may automatically update the "my patients list" to add and remove throughout the course of the day as patients are admitted to, transferred from, and discharged from the inpatient unit. Additionally, a nurse and/or other health care professional may create his or her own list of patients.

In another embodiment, the bi-directional interface system may generate a list of patients for a non-nursing healthcare professional based on a qualifier. This qualifier may be outside of the patient's unit, such as the service or referral. The non-nursing professional would be able to have a list that is specific to his or her own assignment.

The bi-directional interface system may automatically synthesize personal health information and data extracted from the patient's electronic health record and/or ancillary systems and organized in a meaningful manner, relevant to the patient population. Accordingly, the system, via a mobile application, may display the patient information needed for safe handoffs of patients from one nurse to the next during the shift, and as such, may generate a report for the nurse. This report is generated by the system to provide a customizable display of patient information, which may be at the inpatient unit level, which is consistent across multiple caregivers. As such, the system may access the patient information available within the patient's EHR and/or ancillary systems, and may display such information via a mobile device, without storing any of the information on the mobile device itself. The system may automatically update this dynamic personal health information, as updates are made to the electronic health record itself. The same format may be used by other health care professionals. The health care professionals may receive a report on their patients from another member of his or her team and maintain that report with him or her until handing over care responsibility to the next individual.

Additionally, the system may generate a customized report of patient information that has changed from a set period of time designed according to the unit and/or health care professional role. For example, a nurse that cared for the patient yesterday may not need to be updated with the entire report from the reporting module. Instead, the updates will provide the nurse with the information that has changed in a designated time frame.

The system may also facilitate orders integration and notifications, which allows for orders to be interfaced in real time at a set interval. Accordingly, the system may automatically generate notifications to be sent to the user when new orders or labs (for example) are available for patients. The system may also generate notifications of orders requiring immediate attention.

In another aspect, the system may provide an allergies interface, which may display allergies that are recorded in a patient's EHR. The system may automatically update the allergies that are transmitted and displayed on the mobile device, as they are updated externally on a patient's EHR. Additionally, the system may provide a lab results interface, which may provide nurses with access to recent lab results on their mobile devices. The system may interface with ancillary systems to automatically update the lab results that are transmitted and displayed on the mobile device, as they are updated in ancillary systems.

In another aspect, the system may provide an images interface, which may display images that are taken with the mobile device or previously stored images. The system may take images with the mobile device and transmit the image into the patient's EHR or other ancillary information system to update the database with the taken images.

In another aspect the system may generate an electronic schedule of activities (or "To-Do" list) for nurses and other health care professionals to complete for their patients, which electronically organizes a nurse's and/or other health care professionals schedule of activities for his or her assigned patients for the day. The schedule may include whether a patient needs a medication, dressing change, diagnostic tests or other treatments. Accordingly, the system may seamlessly interact with the electronic health record system and other ancillary systems to retrieve information pertinent to generate such a schedule, as the scheduling module may be integrated with such external systems. Additionally, the nurse and/or other health care professional may manually input entries into his or her schedule. The system may allow a nurse and/or other health care professional to free text in a list of "To-Dos" for a patient. The manual entry allows for the nurse and/or health care provider to modify their own list in a way that fits with their individual cognitive workflow that cannot be captured in an electronic organization for each individual nurse and/or health care professional.

The bi-directional interface system may also facilitate data entry, which may be ultimately fed into an external electronic health record system and as such is incorporated into a patient's EHR. The system will interface with the hospital EHR system for real time updating of patient information that may be inputted via a mobile device. As such, personal health information may automatically be transmitted by the system into the electronic health record, which will provide immediate access to these values for those who have access to the electronic health record. The data that may be inputted may include, but is not limited to, vital signs and intake and output ("I/O") values. Specifically, the vital signs may include heart rate, blood pressure, respiratory rate, temperature, pulse oxygen level, and/or oxygen requirements. The intake values may relate to oral intake, NG/OG/PG (intake through a tube that goes to the gastrointestinal system), and/or IV intake. The output value may relate to urine and/or stool.

The bi-directional interface system may allow short messages or "notes" which may be recorded in an unstructured text formation to be passed between and accessed by multiple caregivers, and transmitted to the patient's electronic health record for reference.

In another embodiment, the bi-directional interface system may include a data trending module. During the delivery of patient care, patients will occasionally have unusual results that prompt the nurse and other health care professionals to evaluate whether those results fall within the patient's individual norms for values. The system may provide trending capabilities, and may interface with ancillary systems, for the nurse to view the patient's trends of each vital sign as well as the intake, output and overall fluid balance.

In yet another embodiment, the bi-directional interface system may include a medication administration record module, which may integrate with a patient's medications administration record, such that the system will allow a nurse to be able to view the schedule of medications, reschedule, administer and view the specific order details. The medication administration record contains all medications the patient has ordered for him or her to be administered either on a regular schedule or on an "as needed" schedule.

The bi-directional interface system may contain a server that will be the "bridge" server between the system's mobile application and the EHR system, and it may store application specific settings. The system may access the patient information available within the patient's EHR and/or other ancillary systems, and may display such information via a mobile device, without storing any of the information on the mobile device itself. The system may include an application that may communicate/login into existing enterprise authentication active directory (ADAM/LDAP) via push notification services hosted on a system server. The transactions may be facilitated via a secure socket layer SSL/HTTPS/AES 256 encrypted communications. The system server may host vital back-end services for the system application and also hosts local relational database management system (RDBMS) which may include Oracle or (Oracle's MySQL); the majority of the back-end services may be on the REST/ful protocols. After successful authentication from the system application, the system application may fire AJAX (Asynchronous JavaScript and XML) calls to the existing EHR systems to retrieve relevant information. The EHR system may leverage relational database management systems and may provide asynchronous alerts (push notifications) for Labs/Orders/Other via a "system rules engine" service endpoints. The push notification services may be communicated via a system rules engine into the System Server. A message may be created into RDBMS, and then the system server may create a global unique identifier ("GUID") for that specific message. This will prevent any personal health information ("PHI") message from going outside of the firewall and not achieved on any external servers. The push notification services payload may be sent outside of the firewall to push it into a user's device; no PHI is sent and only GUID is sent with the payload. For example, Apple Push Notification Services "APNS" may push the notifications to the appropriate devices and if the device is within the internal firewall then it can look up the message by communication with the system push notification services (hosted on the system server).

The embodiments may take the form of a hardware embodiment, a software embodiment, or an embodiment combining software and hardware. The bi-directional interface system software application may be installed on a user's mobile device. In one embodiment, the present invention takes the form of a computer-program product that includes computer-useable instructions embodied on one or more computer-readable media. The various bi-directional interface system techniques, methods, and systems described herein can be implemented in part or in whole using computer-based systems and methods. Additionally, computer-based systems and methods can be used to augment or enhance the functionality described herein, increase the speed at which the functions can be performed, and provide additional features and aspects as a part of or in addition to those described elsewhere in this document. Various computer-based systems, methods and implementations in accordance with the described technology are presented below.

Referring to the bi-directional interface system 100 shown in FIG. 1, in an embodiment, the centralized server 110, the customization module 101, security module 102, reporting module 103, scheduling module 104, data trending module 105, medication administration record module 106, updates module 113, notes module 114, allergies module 120, and images module 140, may include a general-purpose computer and can have an internal or external memory for storing data and programs such as an operating system (e.g., DOS, Windows 2000™, Windows XP™, Windows NT™, OS/2, UNIX or Linux) and one or more application programs. Examples of application programs include computer programs implementing the techniques described herein for lyric and multimedia customization, authoring applications (e.g., word processing programs, database programs, spreadsheet programs, or graphics programs) capable of generating documents or other electronic content; client applications (e.g., an Internet Service Provider (ISP) client, an e-mail client, or an instant messaging (IM) client) capable of communicating with other computer users, accessing various computer resources, and viewing, creating, or otherwise manipulating electronic content; and browser applications (e.g., Microsoft's Internet Explorer) capable of rendering standard Internet content and other content formatted according to standard protocols such as the Hypertext Transfer Protocol (HTTP). One or more of the application programs can be installed on the internal or external storage of the general-purpose computer. Alternatively, in another embodiment, application programs can be externally stored in or performed by one or more device(s) external to the general-purpose computer. In an embodiment, the customization module 101, security module 102, reporting module 103, scheduling module 104, data trending module 105, medication administration record module 106, updates module 113, notes module 114, allergies module 120, and images module 140 may be application programs.

In addition, client device 107 may be or can include a desktop computer, a server, a laptop computer or other mobile computing device, a network-enabled cellular telephone (with or without media capturing/playback capabilities), wireless email client, or other client, machine or device to perform various tasks including Web browsing, search, electronic mail (email) and other tasks, applications and functions.

The general-purpose computer may include a central processing unit (CPU) for executing instructions in response to commands, and a communication device for sending and receiving data. One example of the communication device is a modem. Other examples include a transceiver, a communication card, a satellite dish, an antenna, a network adapter, or some other mechanism capable of transmitting and receiving data over a communications link through a wired or wireless data pathway.

The general-purpose computer may also include an input/output interface that enables wired or wireless connection to various peripheral devices. Examples of peripheral devices include, but are not limited to, a mouse, a mobile phone, a personal digital assistant (PDA), a keyboard, a display monitor with or without a touch screen input, and an audiovisual input device. In another implementation, the peripheral devices may themselves include the functionality of the general-purpose computer. For example, the mobile phone or the PDA may include computing and networking capabilities and function as a general purpose computer by accessing a network and communicating with other computer systems. Examples of a network, such as network 108, include the Internet, the World Wide Web, WANs, LANs, analog or digital wired and wireless telephone networks (e.g., Public Switched Telephone Network (PSTN), Integrated Services Digital Network (ISDN), and Digital Subscriber Line (xDSL)), radio, television, cable, or satellite systems, and other delivery mechanisms for carrying data. A communications link can include communication pathways that enable communications through one or more networks.

In one implementation, a processor-based system of the general-purpose computer can include a main memory, preferably random access memory (RAM), and can also include a secondary memory. The secondary memory can include, for example, a hard disk drive or a removable storage drive, representing a floppy disk drive, a magnetic tape drive, an optical disk drive (Blu-Ray, DVD, CD drive), magnetic tape, paper tape, punched cards, standalone RAM disks, Iomega Zip drive, etc. The removable storage drive can read from or write to a removable storage medium. A removable storage medium can include a floppy disk, magnetic tape, optical disk (Blu-Ray disc, DVD, CD) a memory card (CompactFlash card, Secure Digital card, Memory Stick), paper data storage (punched card, punched tape), etc., which can be removed from the storage drive used to perform read and write operations. The removable storage medium can include computer software or data.

In alternative embodiments, the secondary memory can include other similar means for allowing computer programs or other instructions to be loaded into a computer system. Such means can include, for example, a removable storage unit and an interface. Examples of such can include a program cartridge and cartridge interface (such as the found in video game devices), a removable memory chip (such as an EPROM or PROM) and associated socket, and other removable storage units and interfaces, which allow software and data to be transferred from the removable storage unit to the computer system.

In one embodiment, network 108 can also include a communications interface that allows software and data to be transferred between client device 107, centralized server 110, the other components shown in system 100, and the ancillary system 111 and associated EHR system 112. The customization module 101, security module 102, reporting module 103, scheduling module 104, data trending module 105, and medication administration record module 106 may also be stand-alone components that can communicate with each other, the centralized server 110, and/or the client device 107 over network 108. Examples of communications interfaces can include a modem, a network interface (such as, for example, an Ethernet card), a communications port, and a PCMCIA slot and card. Software and data transferred via a communications interface may be in the form of signals, which can be electronic, electromagnetic, optical or other signals capable of being received by a communications interface. These signals may be provided to a communications interface via a channel capable of carrying signals and can be implemented using a wireless medium, wire or cable, fiber optics or other communications medium. Some examples of a channel can include a phone line, a cellular phone link, an RF link, a network interface, and other suitable communications channels.

In this document, the terms "computer program medium" and "computer readable medium" are generally used to refer to media such as a removable storage device, a disk capable of installation in a disk drive, and signals on a channel. These computer program products may provide software or program instructions to a computer system. The bi-directional interface system software application may be installed on a user's mobile device.

Computer-readable media include both volatile and non-volatile media, removable and non-removable media, and contemplate media readable by a database, a switch, and various other network devices. Network switches, routers, and related components are conventional in nature, as are means of communicating with the same. By way of example, and not limitation, computer-readable media include computer-storage media and communications media.

Computer-storage media, or machine-readable media, include media implemented in any method or technology for storing information. Examples of stored information include computer-useable instructions, data structures, program modules, and other data representations. Computer-storage media include, but are not limited to RAM, ROM, EEPROM, flash memory or other memory technology, CD-ROM, DVD, holographic media or other optical disc storage, magnetic cassettes, magnetic tape, magnetic disk storage, and other magnetic storage devices. These memory components can store data momentarily, temporarily, or permanently.

Communications media typically store computer-useable instructions—including data structures and program modules—in a modulated data signal. The term "modulated data signal" refers to a propagated signal that has one or more of its characteristics set or changed to encode information in the signal. An exemplary modulated data signal includes a carrier wave or other transport mechanism. Communications media include any information-delivery media. By way of example but not limitation, communications media include wired media, such as a wired network or direct-wired connection, and wireless media such as acoustic, infrared, radio, microwave, spread-spectrum, and other wireless media technologies. Combinations of the above are included within the scope of computer-readable media.

Computer programs which may be associated with applications of the customization module 101, security module 102, reporting module 103, scheduling module 104, data trending module 105, medication administration record module 106, updates module 113, notes module 114, allergies module 120 and images module 140 (also called computer control logic) may be stored in the main memory or secondary memory. Such computer programs can also be received via a communications interface. Such computer programs, when executed, may enable the computer system to perform the features as discussed herein. In particular, the computer programs, when executed, may enable the processor to perform the described techniques. Accordingly, such computer programs may represent controllers of the computer system.

In an embodiment where the elements are implemented using software, the software can be stored in, or transmitted via, a computer program product and loaded into a computer system using, for example, a removable storage drive, hard drive or communications interface. The control logic (software), when executed by the processor, may cause the processor to perform the functions of the techniques described herein.

In another embodiment, the elements may be implemented primarily in hardware using, for example, hardware components such as PAL (Programmable Array Logic) devices, application specific integrated circuits (ASICs), or other suitable hardware components. Implementation of a hardware state machine so as to perform the functions described herein will be apparent to a person skilled in the relevant art(s). In yet another embodiment, elements may be implanted using a combination of both hardware and software.

In another embodiment, the computer-based methods can be accessed or implemented over the World Wide Web by providing access via a Web Page to the methods described herein. Accordingly, the Web Page may be identified by a Universal Resource Locator (URL). The URL may denote both a server and a particular file or page on the server. In this embodiment, it is envisioned that a client computer system, which may be the client device 107, may interact with a browser to select a particular URL, which in turn may cause the browser to send a request for that URL or page to the server identified in the URL. Typically, the server may respond to the request by retrieving the requested page and transmitting the data for that page back to the requesting client computer system, which may be the client device 107 (the client/server interaction may be typically performed in accordance with the hypertext transport protocol or HTTP). The selected page may then be displayed to the user on the client's display screen. The client can then cause the server containing a computer program to launch an application, for example, to perform an analysis according to the described techniques. In another implementation, the server can download an application to be run on the client to perform an analysis according to the described techniques.

Referring to FIG. 1, the bi-directional interface system 100 may include a centralized server 110, a security module 102, a customization module 101, a reporting module 103, a scheduling module 104, a data trending module 105, a medication administration record module 106, an updates module 113, a notes module 114, an allergy module 120 and an images module 140. The centralized server 110, security module 102, customization module 101, reporting module 103, scheduling module 104, data trending module 105, medication administration record module 106, updates module 113, and notes module 114, electronic health record system 112 and ancillary systems 111 may be integrated with each other. The system may dynamically extract patient data from an associated electronic health record repository of an electronic health record system 112 and/or other ancillary systems 111. This patient data may include, but is not limited to, vital signs and/or intake and output values. Accordingly, the system may generate visual displays of the patient data on a mobile device. The system may automatically update the patient data displayed on the mobile device as said data is updated in said associated electronic health record system and/or other ancillary systems. Furthermore, the system may transmit patient data that is inputted in the application on the mobile device to the associated electronic health record repository in real time. The patient data that that is inputted in the application on the mobile device may include, but is not limited to vital signs and/or intake and output values, and notes.

The system may include a security module 102 that securely transmits the patient data over a network. The system's technical architecture is designed in such a way to minimize potential breaches in privacy and security of personal health information. As such, the system may access the patient information available within the patient's EHR and/or other ancillary systems, and may display such information via a mobile device, without storing any of the information on the mobile device itself. The system prevents any personal health information messages from going outside of the firewalls (external, internal, and data). Additionally, a customization module 101 may be utilized to select the specific types of patient data to be extracted from EHR and ancillary systems at a unit level and/or based on the health care professional role. The bi-directional interface system may include a reporting module 103, which may generate a comprehensive report of said patient information for the nurse and/or the other health care professionals.

The system may also include an updates module 113, which may generate a customized report of patient information that has changed from a set period of time for the nurse and/or the other health care professionals. For example, a nurse that cared for the patient yesterday may not need to be updated with the entire report from the reporting module. Instead, the updates will provide the nurse with the information that has changed in a designated time frame.

The system may include a scheduling module 104, which generates and electronically organizes a nurse's schedule of activities. The scheduling module may also be used to generate and electronically organize other health care professionals' schedules of activities. The bi-directional interface system may also seamlessly transmit messages that are inputted in the application on said mobile device to said associated electronic health record repository. The system may display dynamically updated orders, allergies, and/or lab results from ancillary systems 111 and/or EHR systems 112. The system may automatically generate notifications when orders, which may include, but is not limited to x-rays, medication changes, procedures, are to be placed on the patient. As such, a user of the system is not required to actively access the patient's EHR for orders in the computerized provider order entry system ("CPOE"), as users are able to access patient orders from a mobile device. The system may display the orders at determined time intervals, and the orders may be displayed in reverse chronological order. Displaying the orders in reverse chronological order allows the user to view the most recent at the top of the screen and scroll down for those that are older in chronological time. Notification capabilities may be enabled to provide a "push" technology to the nurse and/or other health care professional to notify him or her of new orders that get placed on the patient.

Additionally, a user of the system may be able to access recent lab results from a mobile device. The system may display lab results at determined time intervals in reverse chronological order. Displaying the lab results in reverse chronological order allows the user to view the most recent results at the top of the screen and scroll down for those that are older in chronological time. Notification capabilities may be enabled to provide a "push" technology to the nurse and/or other health care professional to notify him or her of new lab results that get posted to the patient. As such, this notification feature can for example, eliminate the need for the nurse to actively seek out of "pull" the information from the results reporting application over the course of the day.

The system may also include a notes module 114, which may be utilized by a user to generate notes to communicate personal aspects about an individual patient's care. These personal care needs may be directed to a patient's personal preferences, care routines at home, as well as reducing any potential fears or anxieties associated with hospitalizations. These personal care needs may include, but are not limited to a patient's need for liquid medications over tablets or capsules, that a patient is fearful of people in white coats that enter the room, and that the family of a patient prefers that syringes remain in packages before entering the patient's room. The notes module 114 allows a user to enter short messages that will be saved as reminders of these individual care needs. The addition of these short messages allows users to make notations of something specific to a patient's hospitalization, experience that day or experience during a procedure, and these notes may serve as reminders available via a mobile device. These messages may be recorded in an unstructured text formation. Additionally the system may automatically transmit these notes to a patient's EHR.

The bi-directional interface system may include a data trending module 105, which interfaces with ancillary systems 111 and/or EHR systems to generate trends of patient data. For example, based on a patient's vital signs and intake and output, the system may provide trending capabilities to generate and display the patient's trends of each vital sign, as well as the intake, output and overall fluid balance on the mobile device. Additionally, the system may include a medication administration record module 106, which is integrated with a patient's medications administration record. The medication administration record module 106 may generate and display a schedule of medications and/or order details on the mobile device. The system may display the schedule of times in which a medication is due, the dose, the name, the route, the patient and any other details that may be beneficial for a nurse or other health care professional to be aware of. This module may also indicate when and by whom a medication is administered.

Figure 2:
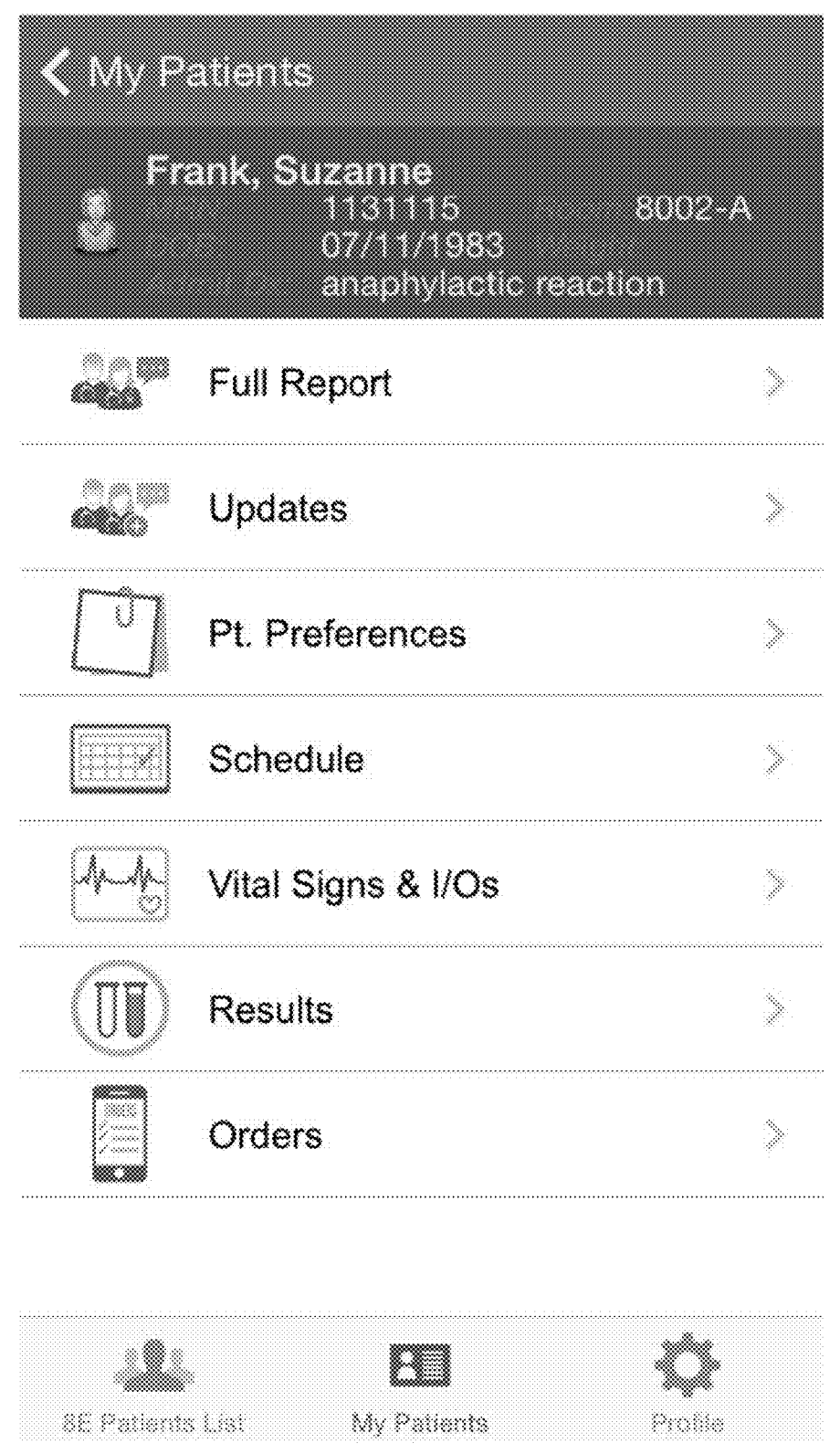

Referring to FIG. 2, the system seamlessly interfaces with existing EHR systems and/or other ancillary systems to automatically extract the information needed to provide care to a patient, and may display such information on a mobile device. Accordingly, the system may display data that exists in the EHR that would be valuable to easily view at a glance (e.g., vital signs, weight, last void) data, as well as facilitate data entry that would interface into the EHR (e.g., vital signs and intake and output). Accordingly, the system may standardize the information available to nurses and other health care professionals at the critical time of handoffs and reduce the nurse's and/or other health care professional's individual need to rely on memory, handwritten notes, and reduce the opportunity for missed or erroneous exchange of information. Furthermore, the system may provide an accessible mobile application to view and enter pertinent patient data to reduce the potential for delayed information and delayed treatments of care. As a result, the nurses and other health care professionals will have the potential for improved accuracy, efficiency, and timeliness of patient information for safe patient care.

Figure 3:
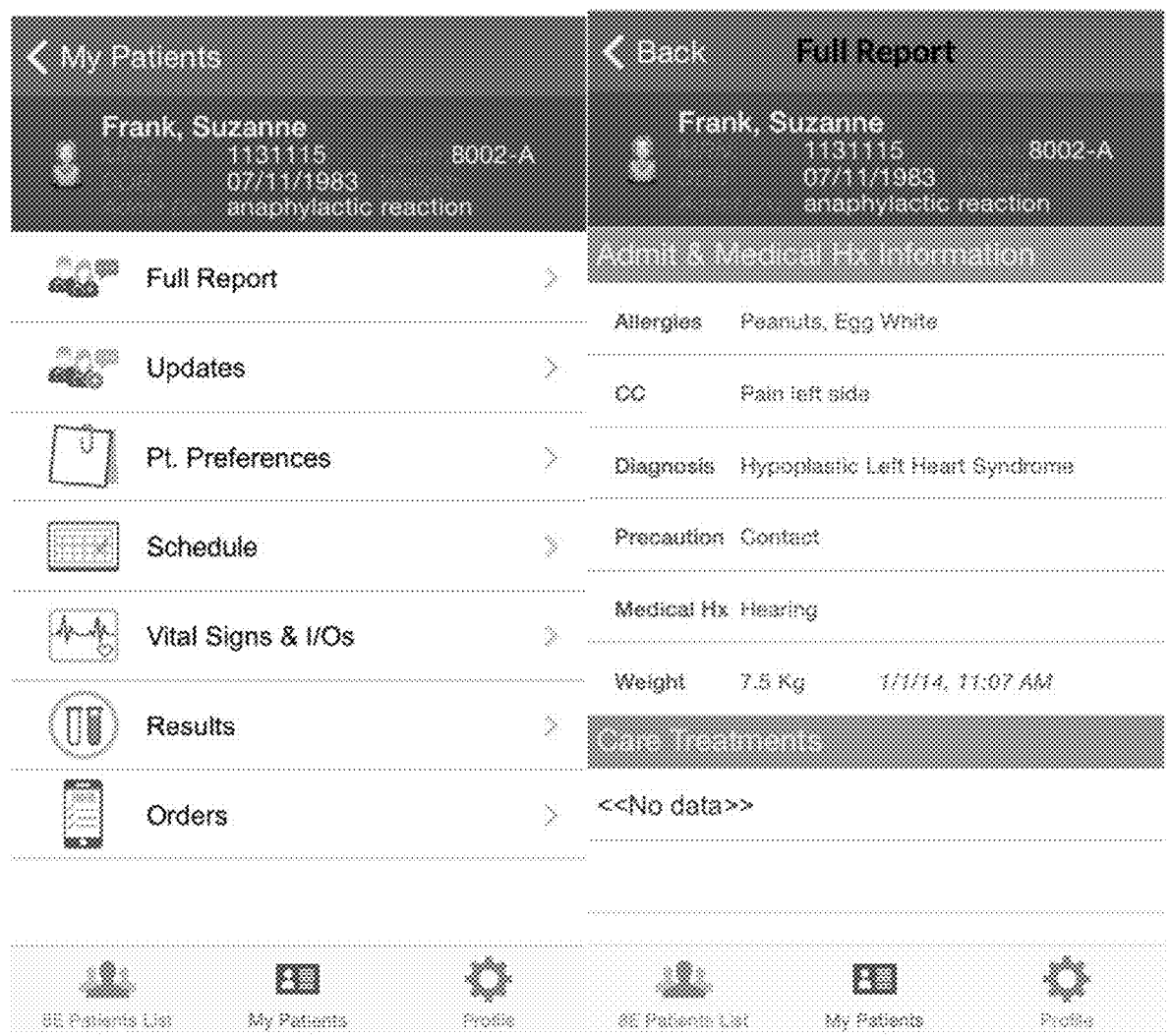
FIG. 3 depicts a visual representation of the generation of a comprehensive nursing report.

Referring to FIG. 3, the bi-directional interface system may include a reporting module 103, which may generate a comprehensive report of said patient information at the unit level and/or health care professional role. This report is generated by the system to provide a customizable display of patient information, which may be at the inpatient unit level, which is consistent across multiple caregivers. As such, the system may access the patient information available within the patient's EHR, and may display such information via a mobile device, without storing any of the information on the mobile device itself. The system may automatically update this dynamic personal health information onto the device, as updates are made to the electronic health record itself.

Figure 4:
FIG. 4 depicts a visual representation of a generated unit census list and patients list.

Referring to FIG. 4, the system may generate a list of admitted patients on an inpatient care unit for the nurse and/or other health care professional. This list may include a list of a nurse's and/or other health care professionals assigned patients from a nursing unit census list. As such, the system may generate and display a list of admitted patients on the nurse's inpatient care unit. Additionally, a nurse and/or other health care professional may manually create such a list. The system may also generate an individual "my patients" list of the assigned patients for the day from the nursing unit census list. The unit census list may include the complete census for the unit and some basic patient level data, which may include patient name, medical record number ("MRN"), and room number. The unit census list may be utilized by the system to automatically to create the individual nurse's list of assigned patients. The system may automatically update the "my patients" list to add and remove throughout the course of the day as patients are admitted to, transferred from, and discharged from the inpatient unit. Additionally, a nurse may manually formulate his or her own patient list.

Figure 5:
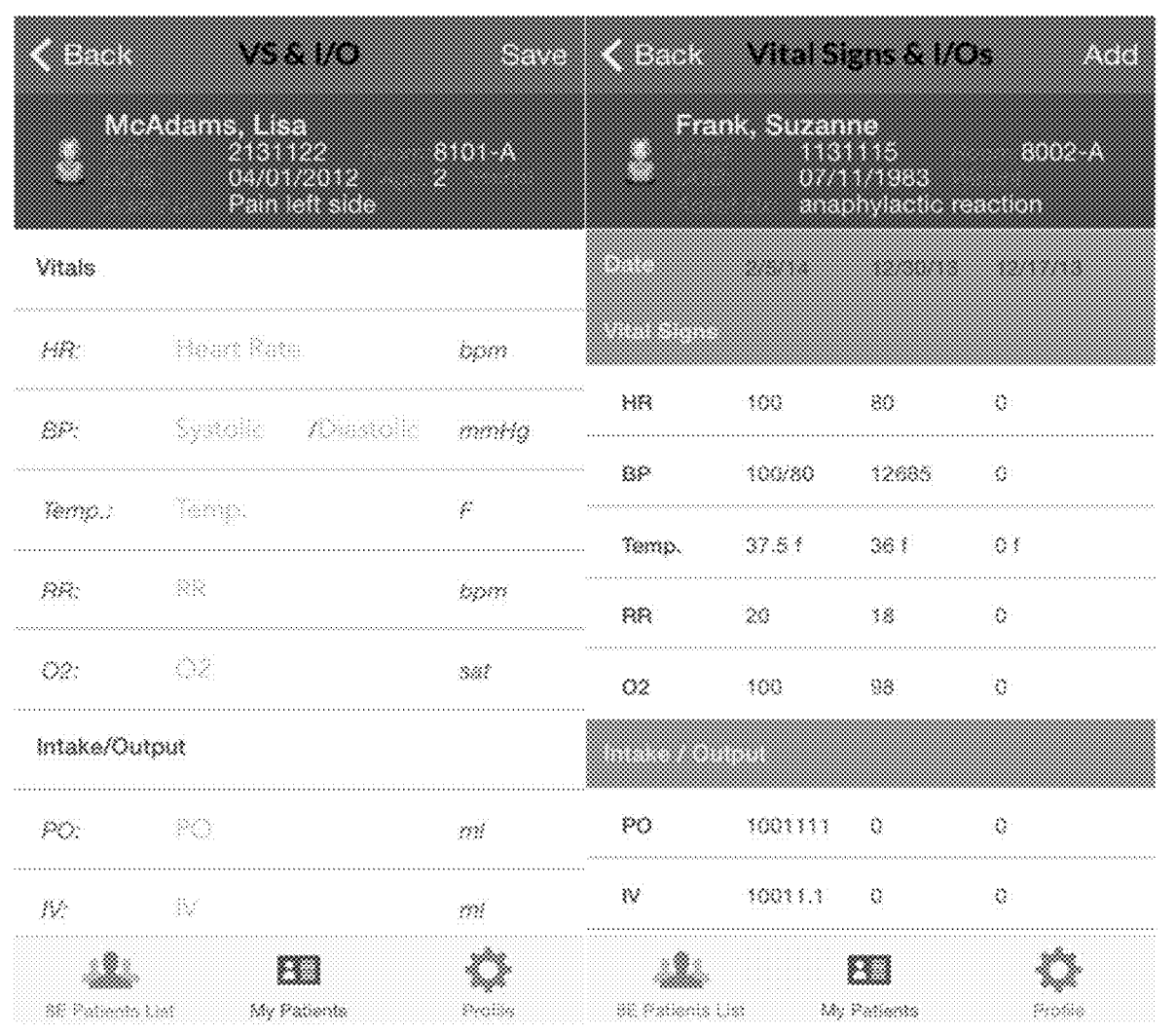

Referring to FIG. 5, the system may generate a vital signs entry view and a vital signs display view for a patient. As such, the system may generate and display a list of vital signs for a patient. Additionally, a nurse and/or other health care professional may manually enter vital signs into the system. The vital signs module may be utilized by the nurse and/or other health care professional to manage health information throughout the patient's visit.

Figure 6:
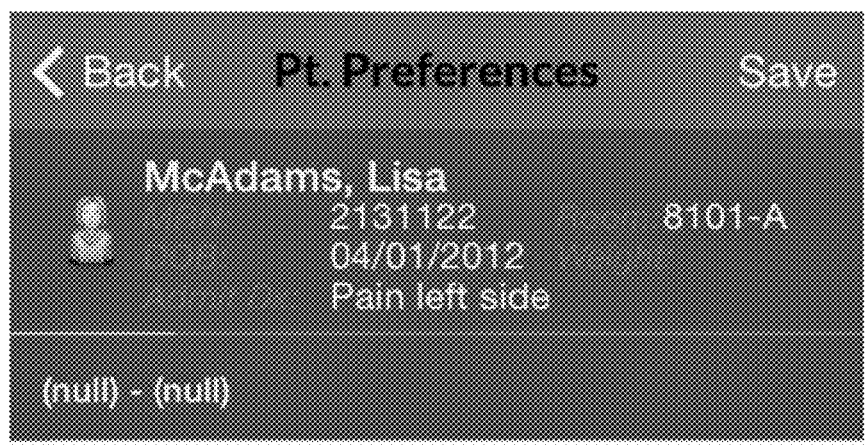
FIG. 6 depicts a visual representation a notes view.
Figure 6:
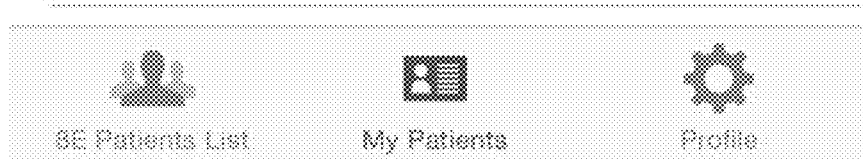
Figure 7:
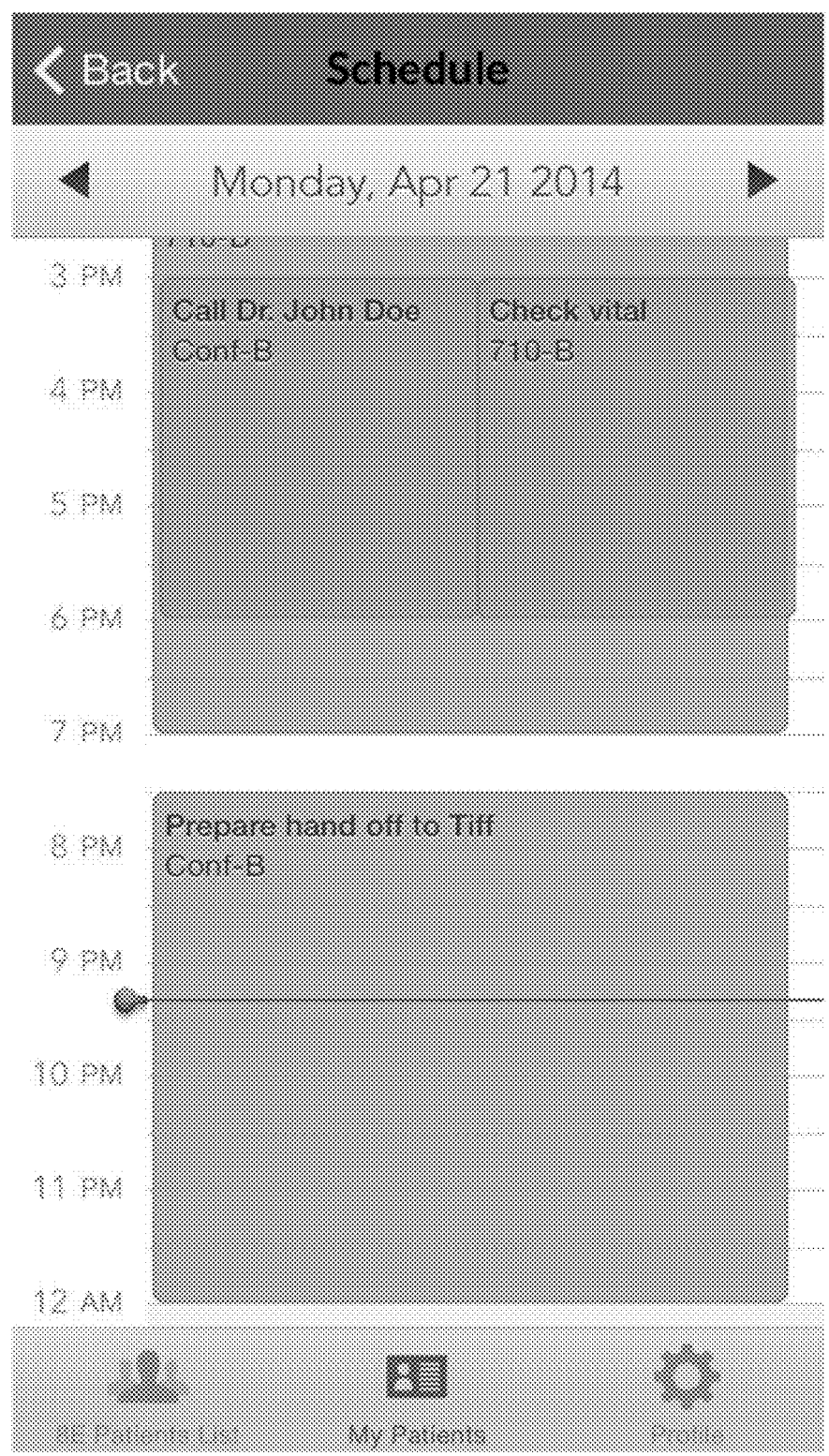
FIG. 7 depicts a visual representation of a schedule view.

Referring to FIG. 6, the system may generate a notes view for a patient. As such, the system may generate and display text based notes for a patient. The nurse and/or other health care professional may manually enter and/or dictate notes into the system that can be interfaced into the EHR system and/or other ancillary systems. The nurse and/or other health care professional may also view the previously entered notes from the system for the patient. The notes module may be utilized by the nurse and/or other health care professional to manage health information throughout the patient's visit.

From the foregoing, it will be seen that this invention is one well adapted to attain all the ends and objects set forth above, together with other advantages, which are obvious and inherent to the system and method. It will be understood that certain features and sub-combinations are of utility and may be employed without reference to other features and sub-combinations. This is contemplated and within the scope of the appended claims.

The invention claimed is:

1. A bi-directional interface system comprising:
    a centralized server;
    one or more mobile devices;
    a network;
    a communications interface located on the centralized server capable of receiving extracting data, the communications interface including a network interface configured to transfer the data received extracted by the communications interface;
    a security module implemented by the centralized server;
    a customization module implemented by the centralized server;
    an updates module implemented by the centralized server; and
    a notes module implemented by the centralized server;
    wherein the bi-directional interface system includes a push notification pull feature hosted on the system centralized server that is implemented by the communications interface;
    the push notification pull feature utilizes the communications interface and network interface to collecting dynamically extracted extract types of patient data of at least one of a plurality of patients from an associated electronic health record repository of an electronic health record system (EHR) and/or and ancillary systems via the network;
    the dynamically extracted types of patient data including updated orders, allergies, and/or lab results from the ancillary systems and/or and EHR system;
    the for which bi-directional interface system implements the updates module to automatically generate notifications and generate visual displays of said dynamically extracted patient data that is pushed to and displayed on the one or more mobile devices;
    the one or more mobile devices receives facilitates data entry for a particular patient that would is transmitted to the note module and is pushed to interface into the associated electronic health record repository by the updates module;
    the updates module automatically updates said patient data displayed on the one or more mobile devices as said patient data is updated and said data entry is pushed to said associated electronic health record system and/or and ancillary systems; and
    wherein said notes module seamlessly transmits the patient data that is inputted on said one or more mobile devices to said associated electronic health record repository in real time;
    the security module is implemented to securely transmit said patient and inputted data over the network without requiring storing allowing storage of any of the patient or inputted data on the one or more mobile devices,
    the technical architecture of the system structured such that the patient information that is viewed displayed and transmitted through the system does is not stored onto any of the one or more mobile devices, and remains stored in the associated electronic health record and ancillary systems;
    wherein the customization module selects the types of patient data to be extracted based on input received from one of a plurality of users of the bi-directional interface system;
    wherein the customization module receives input from one or another of the plurality of users of the bi-directional interface system indicating a shift and/or an associated role as a nurse and/or other health care professional and/or the patient, and the input indicating data points reflecting said types of patient data to be monitored during a designated time frame;
    wherein the updates module generates a customized report of the types of patient information that have changed during the designated time frame for nurses and/or other health care professionals and/or the patient based on the associated role of the user or the plurality of users and the indicated shift information; and
    wherein the notes module automatically receives from the user or the plurality of users and transmits personal care notes to said associated electronic health record repository; and
    wherein the centralized server, security module, customization module, electronic health record system and ancillary systems are integrated with each other.

2. The bi-directional interface system of claim 1 wherein the customization module selects types of patient data to be extracted based on a patient care unit.

3. The bi-directional interface system of claim 1 wherein the customization module selects types of patient data to be extracted based on a role of a health care professional or the role of the patient.

4. The bi-directional interface system of claim 1 wherein said patient data comprises vital signs and/or intake and output values.

5. The bi-directional interface system of claim 1 comprising a reporting module wherein said reporting module generates a comprehensive report of said patient information for nurses and/or other health care professionals and/or the patient.

6. The bi-directional interface system of claim 1 wherein the system generates a list of admitted patients on a nurse's inpatient care unit.

7. The bi-directional interface system of claim 1 wherein the system generates a list of a nurse's assigned patients from a nursing unit census list.

8. The bi-directional interface system of claim 1 comprising a scheduling module wherein said scheduling module generates and electronically organizes a nurse's schedule of activities or a patient's schedule of activities.

9. The bi-directional interface system of claim 1 wherein the system generates a list of patients for a non-nursing healthcare professional based on a qualifier.

10. The bi-directional interface system of claim 9 wherein the qualifier is a service.

11. The bi-directional interface system of claim 9 wherein the qualifier is a referral.

12. The bi-directional interface system of claim 1 comprising a scheduling module wherein said scheduling module generates and electronically organizes a non-nursing healthcare professional's schedule of activities.

13. The bi-directional interface system of claim 1 wherein said system generates notifications when new orders are posted to a patient.

14. The bi-directional interface system of claim 1 wherein said system generates notifications when new lab results are posted to a patient.

15. The bi-directional interface system of claim 1 wherein said patent data that is inputted on the mobile device comprises vital signs and/or intake and output values.

16. The bi-directional interface system of claim 1 wherein said system seamlessly transmits messages that are inputted on said mobile device to said associated electronic health record repository through an interface.

17. The bi-directional interface system of claim 1 wherein said system displays dynamically updated orders, allergies and/or lab results from ancillary systems to an application of said mobile device.

18. The bi-directional interface system of claim 1 comprising a data trending module wherein said module interfaces with ancillary systems to generate trends of patient data on said mobile device.

19. The bi-directional interface system of claim 1 comprising a medication administration record module wherein said module integrates with a patient's medications administration record to generate and display a schedule of medications and/or order details on said mobile device.

20. The bi-directional interface system of claim 1 comprising generating and displaying images on said mobile device.

\* \* \* \* \*